United States Patent [19]

Onopchenko et al.

[11] 4,224,232
[45] Sep. 23, 1980

[54] PRODUCTION OF CARBOXYLIC ACIDS FROM OLEFINS AND MIXTURES OF OLEFINS

[75] Inventors: Anatoli Onopchenko, Monroeville; Johann G. D. Schulz, Pittsburgh, both of Pa.

[73] Assignee: Gulf Research & Development Company, Pittsburgh, Pa.

[21] Appl. No.: 971,707

[22] Filed: Dec. 21, 1978

Related U.S. Application Data

[63] Continuation-in-part of Ser. No. 780,929, Mar. 24, 1977, abandoned, which is a continuation-in-part of Ser. No. 367,176, Jun. 5, 1973, abandoned.

[51] Int. Cl.$^2$ .................................................. C11C 1/00
[52] U.S. Cl. .................................................. 260/413
[58] Field of Search .................................. 260/413 HC

[56] References Cited

U.S. PATENT DOCUMENTS

| | | | |
|---|---|---|---|
| 3,053,869 | 9/1962 | McAlister | 260/413 |
| 3,167,585 | 1/1965 | Anderson | 260/533 |

Primary Examiner—John F. Niebling

[57] ABSTRACT

A process for producing carboxylic acids from olefins having from 20 to 24 carbon atoms or mixtures of olefins having from 20 to 24 carbon atoms which involves adding said olefin or mixtures of said olefins without a solvent to carbon monoxide and sulfuric acid and thereafter adding water to the reaction product so formed.

8 Claims, No Drawings

PRODUCTION OF CARBOXYLIC ACIDS FROM OLEFINS AND MIXTURES OF OLEFINS

This application is a continuation-in-part of our U.S. patent application Ser. No. 780,929, entitled PRODUCTION OF CARBOXYLIC ACIDS FROM OLEFINS AND MIXTURES OF OLEFINS, filed Mar. 24, 1977, abandoned, which, in turn, was a continuation-in-part of our U.S. patent application Ser. No. 367,176, entitled PRODUCTION OF CARBOXYLIC ACIDS FROM OLEFINS AND MIXTURES OF OLEFINS, filed June 5, 1973, abandoned, which applications are incorporated herein by reference.

BACKGROUND OF THE INVENTION

1. Field of the Invention

This invention relates to a process for producing carboxylic acids from olefins having from 20 to 24 carbon atoms or to mixtures containing olefins having from 20 to 24 carbon atoms.

2. Description of the Prior Art

In U.S. Pat. No. 2,831,877 to Koch there is disclosed a process for preparing carboxylic acids which involves reacting olefins and carbon monoxide in the liquid phase without the addition of water and in the presence of acid catalysts containing little or no water, such as sulfuric acid, and thereafter taking up the reaction product in water. Although Koch makes no mention of the effect of a solvent in his process, the reaction involving a lower olefin is carried out, with no seeming preference, with and without a solvent, but with a higher olefin, such as $C_{12}$ or higher, with a solvent, such as paraffins from the Fischer-Tropsch synthesis, or n-hexane. In U.S. Pat. Nos. 3,053,869 to McAlister et al and 3,167,585 to Anderson et al there is no teaching of the problems associated with the treatment of higher olefins in such process to increase selecivities to desired carboxylic acids.

SUMMARY OF THE INVENTION

We have found, unexpectedly, that in the process for preparing carboxylic acids wherein straight chain olefins having from 20 to 24 carbon atoms, or mixtures of straight chain olefins having from 20 to 24 carbon atoms, said olefins being solids at ambient conditions of temperature and pressure, are added to carbon monoxide and sulfuric acid and the reaction product so produced is thereafter hydrolyzed with water, increased selectivities to desired carboxylic acids are obtained if said process is carried out in the absence of a solvent or carrier.

The olefins used herein are straight chain, unbranched olefins, normal alpha olefins as well as internal olefins, preferably normal alpha olefins, having from 20 to 24 carbon atoms, or mixtures of said olefins. When mixtures of said olefins, especially a mixture of normal alpha olefins, are used a typical mixture will consist essentially of about 40 to about 60 weight percent, preferably about 45 to about 55 weight percent, of the $C_{20}$ olefins, from about 30 to about 55 weight percent, preferably about 35 to about 50 weight percent, of the $C_{22}$ olefins and from about five to about 10 weight percent, preferably about six to about nine weight percent, of the $C_{24}$ olefins. Specific examples of olefins that can be used herein include 1-eicosene, 2-eicosene, 3-eicosene, 4-eicosene, 5-eicosene, 6-eicosene, 7-eicosene, 8-eicosene, 9-eicosene, 10-eicosene, 1-heneicosene, 2-heneicosene, 3-heneicosene, 4-heneicosene, 5-heneicosene, 6-heneicosene, 7-heneicosene, 8-heneicosene, 9-heneicosene, 10-heneicosene, 11-heneicosene, 1-docosene, 2-docosene, 3-docosene, 4-docosene, 5-docosene, 6-docosene, 7-docosene, 8-docosene, 9-docosene, 10-docosene, 11-docosene, 1-tricosene, 2-tricosene, 3-tricosene, 4-tricosene, 5-tricosene, 6-tricosene, 7-tricosene, 8-tricosene, 9-tricosene, 10-tricosene, 11-tricosene, 12-tricosene, 1-tetracosene, 2-tetracosene, 3-tetracosene, 4-tetracosene, 5-tetracosene, 6-tetracosene, 7-tetracosene, 8-tetracosene, 9-tetracosene, 10-tetracosene, 11-tetracosene, and 12-tetracosene.

In order to obtain high selectivity to desired carboxylic acid in accordance with the process defined and claimed herein it is imperative that the olefin be added to the reaction zone containing the catalyst, which is also the solvent, and reactant carbon monoxide.

The catalyst used herein can be substantially 100 percent sulfuric acid, although it is preferred that aqueous sulfuric acid having a strength of about 90 to about 99 percent, preferably about 92 to about 98 percent, be used.

The reaction is carried out under mild conditions of temperature and pressure. Thus, the temperature can be in the range of about 0° to about 50° C., preferably about 10° to about 35° C., and the pressure about 100 to about 5000 pounds per square inch gauge (about seven to about 352 kilograms per square centimeter), preferably from about 500 to about 2000 pounds per square inch gauge (about 35.2 to about 140.8 kilograms per square centimeter). Reaction time of about 0.01 to about 12 hours, preferably about 0.1 to about four hours, will suffice.

At the end of the reaction period the reactor is depressured and the reaction product is contacted with water, preferably ice water, to obtain the desired carboxylic acids. The carboxylic acids will form a separate phase on the surface of the reaction mixture and can be recovered therefrom, for example, by decantation. After washing the reaction mixture with water, the recovery of carboxylic acids is best effected by distillation.

Thus, only four components are needed in the reaction zone in accordance with the process defined and claimed herein: the defined olefin or mixtures of defined olefins, carbon monoxide, sulfuric acid and water. In order to obtain the desired conversion at least equimolar amounts of olefins and carbon monoxide are added to sulfuric acid and water then hydrolyzed with water. As noted, in accordance with the process defined and claimed herein, increased selectivities to desired carboxylic acid are obtained when no solvent is present and the reaction is carried out solely with olefin, carbon monoxide, sulfuric acid and water.

As shown in our U.S. Pat. No. 3,842,106, when the olefin used is a normal alpha olefin or a straight chain internal olefin obtained by a disproportionation reaction, the carboxylic acid obtained can be defined as falling within the following two general structures:

Tertiary (Neo) Carboxylic Acids

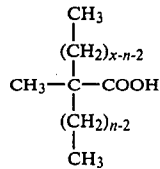

wherein x is the number of carbon atoms in the reactant olefin, that is, from 20 to 24 carbon atoms and n is the integer 2, 3, 4 up to x/2 for even integers between 20 and 24 and 2, 3, 4 up to x+1/2 for odd integers between 20 and 24, and Secondary (Iso) Carboxylic Acids

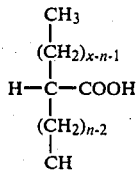

wherein x is as defined above, and n is the integer 2, 3, 4, up to x/2 for even integers between 20 and 24 and 2, 3, 4 up to x+1/2 for odd integers between 20 and 24. About half of the carboxylic acids obtained are tertiary and about half secondary.

DESCRIPTION OF PREFERRED EMBODIMENTS

The process can be understood by reference to the following specific examples.

EXAMPLE I

Into a one-liter, 316-stainless steel, magnetically-stirred autoclave there was charged 534 grams of 96.7 weight percent aqueous sulfuric acid and 180 grams of 1-eicosene. The 1-eicosene used had a melting point of 28° to 29° C. It was added to the autoclave in chunks whose longest dimension was from about one-eighth to about one-quarter inch. The autoclave was pressured to 1000 pounds per square inch gauge (70.5 kilograms per square centimeter) with carbon monoxide and the contents were permitted to react with each other for six hours at 30° C. At the end of the reaction period the pressure was released through a pressure release valve to about 200 pounds per square inch gauge (about 14.1 kilograms per square centimeter) and the total product was then discharged into a vessel containing 1000 grams of a mixture of ice and water maintained at ambient conditions. This resulting mixture was then transferred to a separatory funnel and allowed to settle for about 30 minutes until phase separation occurred. The sulfuric acid layer was withdrawn and the organic layer was then washed with water to remove residual sulfuric acid. Sufficient amount of 7.5 normality sodium hydroxide solution was added to the washed organic layer to obtain a pH of about 6.5. The resulting mixture was permitted to stand for about two hours for phase separation to occur. Again the aqueous phase was withdrawn and the organic layer washed with water. The washed organic layer was subjected to distillation to obtain 96.4 grams of a product having a boiling point of about 210° to about 215° C. at 1.2 millimeters of mercury, corresponding to about a 46 weight percent yield of the desired $C_{21}$ carboxylic acids.

EXAMPLE II

Into the same autoclave used above there was charged 375 grams of 97 percent aqueous sulfuric acid and the autoclave was then pressured with carbon monoxide to 1200 pounds per square inch gauge (84.5 kilograms per square centimeter). While the temperature was maintained at 29° C. there was introduced into the autoclave at a temperature of 25° C. by means of a Milroy pump 160 grams of 1-eicosene dissolved in 85 grams of n-hexane over a period of two hours. After addition of water and work-up as above, analysis of the product by distillation indicated a 45.6 weight percent yield of the desired $C_{21}$ carboxylic acids.

EXAMPLE III

The run of Example I was repeated except that the olefin alone was added gradually to the autoclave over a period of four hours and the reaction was permitted to proceed for an additional two hours. The olefin in the inlet line was kept fluid, prior to injection into the autoclave, by tracing the inlet line outside the autoclave with steam lines. The temperature of the olefin in the inlet line was maintained at about 35° to 45° C. However, when it was pumped into the autoclave through the top, wherein the temperature was maintained around, and preferably below the melting point of the olefin, the olefin immediately solidified into fine particulate form and was dispersed in the random mixture therein. On work-up, as before, a 76 weight percent yield of $C_{21}$ carboxylic acids was obtained. The temperature during the reaction was maintained at 29° to 30° C.

EXAMPLE IV

The procedure employed in Example III was repeated using 440 grams of 97 weight percent sulfuric acid and 222 grams of 1-eicosene. The initial pressure was set at 1350 pounds per square inch gauge (91.8 kilograms per square centimeter) and the temperature was maintained at 45° C. On work-up by distillation a total of 164.9 grams of $C_{21}$ carboxylic acids were formed, representing a yield of 63.8 percent.

EXAMPLE V

Example IV was again repeated except that the temperature was maintained at 35° C. On work-up by distillation a total of 183.0 grams of $C_{21}$ carboxylic acids were formed, corresponding to 70.8 percent yield.

EXAMPLE VI

Example IV was once more repeated except that the temperature was maintained at 25° C. A total of 212.3 grams of $C_{21}$ carboxylic acids were obtained corresponding to an 82.1 percent yield.

EXAMPLE VII

Example IV was further repeated except that the temperature was maintained at 15° C. A total of 206.7 grams of $C_{21}$ carboxylic acids were obtained, representing an 80 percent yield. The data of Examples III through VII are summarized below in Table I, showing surprisingly that higher yields of desired carboxylic acids are obtained at reaction temperatures below the melting point of the olefin.

TABLE I

| Example | Temperature °C. | Percent Yield | Percent Increase of Carboxylic Acids In Continuous Operation Without Solvent (Over Batch Operation of Example I) |
|---------|-----------------|---------------|------------------|
| III | 29-30 | 76.0 | 65.2 |
| IV | 45 | 63.8 | 38.7 |
| V | 35 | 70.8 | 53.9 |
| VI | 25 | 82.1 | 78.3 |
| VII | 15 | 80.0 | 73.9 |

EXAMPLE VIII

The same autoclave used above was charged with 445 grams of a 97 percent aqueous sulfuric acid and 220 grams of a normal alpha olefin mixture (for practical purposes referred to herein as a "$C_{20}$ to $C_{24}$ alpha olefin mixture" of the following composition.

| Alpha Olefin | Weight Percent | Melting Point of Individual Olefin, °C. |
|--------------|----------------|------------------------------------------|
| $C_{18}$ | 3.3 | — |
| $C_{20}$ | 51.0 | 28.6 |
| $C_{22}$ | 37.9 | 41 |
| $C_{24}$ | 7.8 | 46 |

The mixture had a melting point of about 42° to 44° C. The reactor was pressured to 1000 pounds per square inch gauge (70.5 kilograms per square centimeter) with carbon monoxide and the reaction was permitted to proceed for three hours at 28° C. The reaction mixture was taken up in water and worked up as before. Analysis of the product by vapor phase chromatography showed that only 10 weight percent of the product consisted of the desired $C_{19}$-$C_{25}$ carboxylic acids.

EXAMPLE IX

Into the same autoclave used above containing 440 grams of 97 percent aqueous sulfuric acid and under a carbon monoxide pressure of 1350 pounds per square inch gauge (94.4 kilograms per square centimeter) and a temperature of 30° C. there was introduced over a period of four hours 220 grams of the $C_{20}$-$C_{24}$ alpha olefin mixture in 220 grams of cyclohexane, following the procedure of Example II. Reaction was continued for 30 minutes and the reaction product was hydrolyzed with water and worked up as before. A major fraction weighing 141.8 grams was obtained containing $C_{19}$-$C_{25}$ carboxylic acids whose boiling point was in the range of 210° to 230° C. at about 1.0 millimeters of mercury. Based on neutral equivalent determination, this corresponds to a 44 percent yield of desired carboxylic acids.

EXAMPLE X

The run of Example IX was repeated, following the procedure of Example III, except that no cyclohexane was present. Selectivity to desired carboxylic acids was found to be 69 weight percent.

The data obtained in Examples I through III and VIII through X are summarized below in Table II.

TABLE II

| Example | Olefin or Mixtures of Olefin in Field | Melting Point of Olefin or Mixtures of Olefins, °C. | Solvent of Diluent | Mode of Operation | Reaction Temperature °C. | weight Percent Yield of Desired Organic Acid in Product Mixture | Percent Increase of Organic Acid in Continuous Operation Without Solvent or Diluent |
|---------|---------------------------------------|-----------------------------------------------------|--------------------|--------------------|---------------------------|----------------------------------------------------------------|-------------------------------------------------------------------------------------|
| I | $C_{20}$ | 28-29 | None | Batch | 30 | 46 | — |
| II | $C_{20}$ | 28-29 | n-hexane | Incremental Addition | 29 | 45.6 | — |
| III | $C_{20}$ | 28-29 | None | Incremental Addition | 29-30 | 76 | 65 |
| VIII | $C_{20}$-$C_{24}$ | 42-44 | None | Batch | 28 | 10 | — |
| IX | $C_{20}$-$C_{24}$ | 42-44 | Cyclohexane | Incremental Addition | 30 | 44 | — |
| X | $C_{20}$-$C_{24}$ | 42-44 | None | Incremental Addition | 30 | 69 | 56 |

The results obtained herein are most unusual. As noted, the olefins employed herein are solids at ambient conditions of temperature and pressure. It would have been expected, therefore, that it would be necessary to bring these olefins into solution to induce mobility and dispersion necessary for contacting of the sulfuric acid phase with the hydrocarbon phase for ionization and formation of reactive intermediates. The data in Table II show that when the reactions were carried out in batch operations the weight percent of desired organic acids in Example I and in Example VIII were, respectively, 46 weight percent and 10 weight percent. Using the preferred incremental addition in Example II and n-hexane to induce mobility and dispersion of the olefin in the reaction mixture resulted in no improvement in desired organic acid over Example I. However, there was a significant improvement when this was done in Example IX in comparison with Example VIII. However, the weight percent of desired organic acid in Example IX was no different than that obtained in Examples I and II. But note when Examples II and IX were repeated with no solvent or diluent the percent improvement in selectivity to desired organic acid improved significantly in Examples III and X to 65 weight percent and 56 weight percent, respectively. Another unusual phenomenon occurring herein resides in the fact that the reaction temperatures in each of Examples III and X were held near or below the melting point of the olefin or olefin mixture. Comparison of Examples III, IV, V, VI and VII shows the best yields of desired carboxylic acids were obtained when reaction temperatures were maintained below the melting point of the olefin.

The carboxylic acids produced herein can be reacted with a polyalkylene polyamine to obtain a polyamide which can be added to a lubricating oil to improve its pour and detergency characteristics.

Obviously, many modifications and variations of the invention, as hereinabove set forth, can be made without departing from the spirit and scope thereof, and, therefore, only such limitations should be imposed as are indicated in the appended claims.

We claim:

1. A process for the production of carboxylic acids from a straight chain, unbranched normal alpha olefin having from 20 to 24 carbon atoms or mixtures of straight chain, unbranched normal alpha olefins having from 20 to 24 carbon atoms, said olefins being solids at ambient conditions of temperature and pressure, aqueous sulfuric acid of at least 90 percent strength, carbon monoxide and water which comprises heating said olefins to a temperature above the melting point of said olefins and then adding said olefins incrementally in a fine particulate form to a reaction zone wherein the temperature is in the range of about 0° to about 50° C. and the pressure about 100 to 5000 pounds per square inch gauge, containing carbon monoxide and sulfuric acid of at least 90 percent strength, adding water to the reaction product to produce carboxylic acids and thereafter recovering the desired carboxylic acid product.

2. The process of claim 1 wherein said olefin is a $C_{20}$ normal alpha olefin.

3. The process of claim 1 wherein said olefin is a $C_{22}$ normal alpha olefin.

4. The process of claim 1 wherein said olefin is a $C_{24}$ normal alpha olefin.

5. The process of claim 1 wherein said olefin charge is a mixture of olefins having from 20 to 24 carbon atoms.

6. The process of claim 1 wherein the strength of the sulfuric acid is about 90 to about 99 percent.

7. The process of claim 1 wherein the strength of the sulfuric acid is about 92 to about 98 percent.

8. The process of claim 1 wherein the temperature is in the range of about 10° to about 35° C. and the pressure about 500 to about 2000 pounds per square inch gauge.

* * * * *